US006503882B2

(12) United States Patent
Huber et al.

(10) Patent No.: US 6,503,882 B2
(45) Date of Patent: *Jan. 7, 2003

(54) TREATMENT OF HIV

(75) Inventors: Brigitte T. Huber, Boston, MA (US); Tracy Schmitz, Cambridge, MA (US); Robert Underwood, Quincy, MA (US)

(73) Assignee: Trustees of Tufts College, Medford, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/484,640

(22) Filed: Jan. 18, 2000

(65) Prior Publication Data

US 2002/0147130 A1 Oct. 10, 2002

Related U.S. Application Data

(63) Continuation of application No. 08/852,394, filed on May 7, 1997, now Pat. No. 6,100,234.

(51) Int. Cl.[7] .......................... A61K 37/00; A61K 31/40
(52) U.S. Cl. .............................. 514/2; 514/18; 514/408
(58) Field of Search ................................ 514/2, 18, 408

(56) References Cited

U.S. PATENT DOCUMENTS

| | | | |
|---|---|---|---|
| 4,318,904 A | 3/1982 | Shaw et al. | 424/177 |
| 4,443,609 A | 4/1984 | Oude Alink et al. | 548/111 |
| 4,499,082 A | 2/1985 | Shenvi et al. | 514/2 |
| 4,582,821 A | 4/1986 | Kettner et al. | 514/18 |
| 4,636,492 A | 1/1987 | Kettner et al. | 514/18 |
| 4,644,055 A | 2/1987 | Kettner et al. | 530/330 |
| 4,652,552 A | 3/1987 | Kettner et al. | 514/18 |
| 4,935,493 A | 6/1990 | Bachovchin et al. | 530/331 |
| 4,963,655 A | 10/1990 | Kinder et al. | 530/531 |
| 5,093,477 A | 3/1992 | Mölling et al. | 530/328 |
| 5,187,157 A | 2/1993 | Kettner et al. | 514/18 |
| 5,215,926 A | 6/1993 | Etchells, III et al. | 436/501 |
| 5,242,904 A | 9/1993 | Kettner et al. | 514/18 |
| 5,250,720 A | 10/1993 | Kettner et al. | 558/288 |
| 5,288,707 A | 2/1994 | Metternich | 514/19 |
| 5,296,604 A | 3/1994 | Hanko et al. | 546/169 |
| 5,329,028 A | 7/1994 | Ashkenzi et al. | |
| 5,378,624 A | 1/1995 | Berenson et al. | 435/239 |
| 5,384,410 A | 1/1995 | Kettner et al. | 548/405 |
| 5,444,049 A | 8/1995 | de Nanteuil et al. | 514/18 |
| 5,462,928 A | 10/1995 | Bachovchin et al. | 514/19 |
| 5,506,130 A | 4/1996 | Peterson et al. | 435/240.1 |
| 5,527,923 A | 6/1996 | Klingler et al. | 548/570 |
| 5,543,396 A | 8/1996 | Powers et al. | 514/19 |
| 5,554,728 A | 9/1996 | Basava et al. | 530/327 |
| 5,635,386 A | 6/1997 | Palsson et al. | 435/372 |
| 5,635,387 A | 6/1997 | Fei et al. | 435/378 |
| 5,646,043 A | 7/1997 | Emerson et al. | 435/373 |

FOREIGN PATENT DOCUMENTS

| | | |
|---|---|---|
| DE | 158109 | 12/1982 |
| DE | 270382 A1 | 7/1989 |
| DE | 296075 A5 | 11/1991 |
| EP | 0356223 A2 | 2/1990 |
| EP | 0371467 A2 | 6/1990 |
| EP | 0471651 A2 | 2/1992 |
| EP | 0481311 A2 | 4/1992 |
| EP | 0615978 A1 | 9/1994 |
| EP | 0420913 B1 | 11/1995 |
| EP | 0688788 A1 | 12/1995 |
| WO | WO89/03223 | 4/1989 |
| WO | WO91/16339 | 10/1991 |
| WO | WO91/17767 | 11/1991 |
| WO | WO92/12140 | 7/1992 |
| WO | WO92/17490 | 10/1992 |
| WO | WO93/02057 | 2/1993 |
| WO | WO93/05011 | 3/1993 |
| WO | WO93/08259 | 4/1993 |
| WO | WO93/10127 | 5/1993 |
| WO | WO93/16102 | 8/1993 |
| WO | WO94/03055 | 2/1994 |
| WO | WO94/09132 | 4/1994 |
| WO | WO94/20526 | 9/1994 |
| WO | WO94/25873 | 11/1994 |
| WO | WO94/28915 | 12/1994 |
| WO | WO94/29335 | 12/1994 |
| WO | WO95/11689 | 5/1995 |
| WO | WO95/12618 | 5/1995 |
| WO | WO95/15309 | 6/1995 |
| WO | WO9511689 | 7/1995 |
| WO | WO95/29190 | 11/1995 |
| WO | WO95/29691 | 11/1995 |
| WO | WO95/34538 | 12/1995 |
| WO | WO96/40263 | 12/1996 |
| WO | WO96/40858 | 12/1996 |

OTHER PUBLICATIONS

Colowick, S., et al., "Methods in Enzymology", pp. 220–225.

Cordes, E., et al., "Transition States for Hydrolysis of Acetals, Ketals Glycosides, and Glycosylamines", Chapter 11, pp. 429–465.

Thompson, R., "Use of Peptide Aldehydes to Generate Transition–State Analogs of Elastase", *Biochemistry*, (1973), 12:1:47–51.

Baugh, R., et al., "Proteinases and Tumor Invasion", (1980), 165:157–179.

(List continued on next page.)

Primary Examiner—Zohren Fay
(74) Attorney, Agent, or Firm—Choate, Hall & Stewart; Brenda Herschbach Jarrell; C. Hunter Baker (57) ABSTRACT

A method for increasing immune responses of a human patient infected with HIV, involving contacting the T-cells, in vitro or in vivo, with an organic compound at a concentration effective to cause T-cell proliferation, but below an amount that causes detectable cytotoxicity.

17 Claims, 6 Drawing Sheets

OTHER PUBLICATIONS

Bodansky, M., "Principles of Peptide Synthesis", Springer–Verlag, (1984), vol. 16.

Bodansky, M., "The Practice of Peptide Synthesis", Springer–Verlag, (1984), vol. 21.

Matteson, D., et al., "Synthesis and Properties of Pinanediol α–Amido Boronic Esters" *Organometallics,* 1984), 3:1284–1288.

Powers, C., et al., "Elastase Inhibitors for Treatment of Emphysema—NHLBI Workshop Summary" *US Dept. of Health and Human Services,* (1985), 1097–1100.

Yoshimoto, T., et al., "Comparison of Inhibitory Effects of Prolinal–Containing Peptide Derivatives on Prolyl . . . ", (1985), 98:975–979.

Kettner, C.A., et al., "Kinetic Properties of the Binding of Alpha–Lytic Protease to Peptide Boronic Acids", *Biochemistry,* (1988), 27:7682–7688.

Tam, J.P., "Synthetic Peptide Vaccine Design: Synthesis and Properties of High–Density Multiple Antigenic Peptide System", *Proc Natl Acad Sci USA,* (1988), 85:5409–5413.

Bailey, P.D., "An Introduction to Pepetide Chemistry", Wiley Publishers, (1990), 1–81.

Kettner, C.A. and Shenvi, A.B., "Peptide Boronic Acid Inhibitors of Trypsin–Like Proteases, Their Preparation and Use as Anticoagulants and Inflammation Inhibitors", *Chemical Abstracts,* (1980), 112:80(91790c).

Bachovchin, W.W., et al., "Inhibition of IGA1 Proteinases from *Neisseria Gonorrhoeae* and *Hemophilus Influenzae* by Peptide Prolyl Boronic Acids", *J Biol Chem,* (1990), 265: 3738–3743.

Wildenes et al., "Monoclonal Antibodies (mAb) against gp130 Imitating Cytokines Which Use the gp130 for Signal Transduction", (Jul., 1995), p. 303.

Blumenstein et al., Biochem. Biophys. Res. Comm. 163:980–987.

"Update on Viral Pathogenesis," by Ronald B. Luftig et al. ASM News 56:368, 1990.

"Inhibition of Human Immunodeficiency Virus Type I Infection in a T–Cell Line (CEM) by New Dipeptidyl–Peptidase IV (CD26) Inhibitors," J.D. Jiang et al., Res. Virol., 1997, 148, pp. 255–266.

"Structure Activity Relationships of Boronic Acid Inhibitors of Dipeptidyl Peptidase IV. I. Variation of the $P_3$ Position of Xaa –boro Dipeptides," Simon J. Coutts et al., J. Med. Chem, 1996, 39, pp. 2087–2094.

"Generation and Use of Nonsupport–Bound Peptide and Peptidomimetic Combinatorial Libraries,"J.M. Ostresh et al., Methods in Enzymology, vol. 267, chapter 13, edited by John N. Abelson, 1996, Academic Press, San Diego, ISBN 0–12–182168–4.

Kinder, D.H. et al., "Analogues of Carbamyl Aspartate as Inhibitors of Dihydroorotase: Preparation of Boronic Acid Transition–State Analogues and a Zinc Chelator Carbamylhomocysteine", *J Med Chem.* (1980), 33:819–823.

Flentke, G.R., et al., "Inhibition of Dipeptidyl Aminopeptidase IV (DP–IV) by XAA–Boropro Dipeptides and Use of These Inhibitors to Examine the Role of DP–IV in T–Cell Function", *Proc Natl Acad Sci U S A.,* (1981), 88:1556–1559.

Schon, E., et al., "Dipeptidyl Peptidase IV in the Immune System", *Biol* Hoppe–Seyler, (1991) 372:305–311.

Kubota, T., et al., "Involvement of Dipeptidyl Peptidase IV in an In Vivo Immune Response", *Clin Exp Immunol,* (1992), 89:192–197.

Gutheil, W.G., et al., "Separation of L–Pro–DL–Boropro into its Component Diastereomers and Kinetic Analysis of Their Inhibition of Dipeptidyl Peptidase IV. A New Method for the Analysis of Slow, Tight–Binding Inhibition", *Biochemistry,* (1993), 32:8723–8731.

Kelly, T.A., et al., "Immunosuppressive Boronic Acid Dipeptides: Correlation Between Conformation and Activity", *J Am Chem Soc,* (1993), 115:12637–12638.

Songyang, Z., et al., "SH2 Domains Recognize Specific Phosphopeptide Sequences", *Cell,* (1993), 72:767–778.

Subramanyam, M., et al., "Mechanism of HIV–1 TAT Induced Inhibition of Antigen–Specific T Cell Responsiveness", *J Immunol,* (1993), 150:2544–2553.

Demuth, H.U., et al., "Design of (Omega–N–(O–Acyl)Hydroxy Amid) Aminodicarboxylic Acid Pyrrolidides as Potent Inhibitors of Proline–Specific Peptidases", *FEBS Lett,* (1993), 320:23–27.

Janeway, C., et al., "Immunobiology—The Immune System in Health and Disease", *Current Biology LTD,* (1994), Chapter 12, pp. 1–35.

Brady, L., and Dodson, G., "Reflections on a Peptide", *Nature,* (1994), 368:692–693.

Nicola, N, et al., "Guidebook to Cytokines and Their Receptors", Sambrook and Tooze Publication, (1994), pp. 1–257.

Perstorp Biotec Company, "Molecular Biology Catalog", (1994).

Jameson, B.A., et al., "A Rationally Designed CD4 Analogue Inhibits Experimental Allergic Encephalomyelitis", *Nature,* (1994), 368:744–746. Abstract.

Mosmann, T.R., "Cytokine Patterns During the Progression to AIDS", *Science,* (1994), 265:193–194.

Seed, B., "Making Agonists of Antagonists", *Chemistry & Biology,* (1994), 1:125–129.

Austin, D.J., et al, "Proximity Versus Allostery; The Role of Regulated Protein Dimerization in Biology", *Chemistry & Biology,* (1994), 1:131–136.

Sudmeier, J.L., et al., "Solution Structures of Active and Inactive Forms of the DP IV (CD26) Inhibitor Pro–Boropro Determined by NMR Spectroscopy", *Biochemistry,* (1994), 33:12427–12438.

Kubota, T., et al., "Dipeptidyl Peptidase IV (DP IV) Activity in Serum and on Lymphocytes of MRL/Mp–Ipr/Ipr Mice Correlates with Disease Onset", *Clin Exp Immunol,* (1994), 96:292–296.

Snow, R.J., et al., "Studies on Proline Boronic Acid Dipeptide Inhibitors of Dipeptidyl Peptidase IV: Identification of a Cyclic Species Containing a B–N Bond", *J. Am. Chem. Soc,* 116:10860–10869.

Günther, U.L., et al., "Solution Structures of the DP IV (DD26) Inhibitor Val–BoroPro Determined by NMR Spectroscopy", *Magnetic Resonance in Chem,* (1995), 33:959–970.

Subramanyam, M., et al., "CD26, AT–Cell Accessory Molecule Induction of Antigen–Specific Immune–Suppression by Inactivation of CD26: A Clue to the AIDS Paradox?", in *Dipeptidyl Peptidase IV(CD26) in Metabolism and Immune Response,* (1995), Ed. B. Fleischer: 155–162.

Schmitz T, et al., "Potentiation of the Immune Response in HIV–1+ Individuals", *J Clin Invest,* (1996), 97:1545–1549.

Aquila, H.L., et al., "From Stem Cells to Lymphocytes: Biology and Transplantation", *Immune Rev,* (1997), 157:13–40.

Dupont, B., "Immunology of Hematopoietic Stem Cell Transplantation: A Brief Review of its History", *Immun Rev,* (1997), 157:5–12.

Bodansky, M., "Peptide Chemistry, A Practical Textbook", Springer–Verlag, (1988) 1–9.

Boros, L.G., et al., "Fluoroolefin Peptide Isosteres—Tools for Controlling Peptide Conformations", *Tetrahedron Letters,* (1994), 35:6033–6036.

Goodman, M., and Chorev, M., "On the Concept of Linear Modified Retro–Peptide Structures", *Accounts of Chemical Research,* (1979), 12:1–7.

Guichard, G., et al., Partially Modified Retro–Inverso Pseudopeptides as Non–Natural Ligands for the Human Class I Histocompatibility Molecule HLA–A2, *J Med Chem,* (1996), 39:2030–2039.

Jardetzky, T.S., et al., Three–Dimensional Structure of a Human Class II Histocompatibility Molecule Complexed with Superantigen, *Nature,* (1994), 368:711–718.

Zimmerman, D.H., et al.,"A New Approach to T–Cell Activation: Natural and Synthetic Conjugates Capable of Activating T Cells", *Vaccine Res,* (1996), 5:91–102.

Zimmerman, D.H., et al., "Immunization with Peptide Heteroconjugates Primes a T Helper Cell . . . " *Vaccine Res,* (1996), 5:103–118.

Welch, J. L., and Lin, J., Fluoroolefin Containing Dipeptide Isoteres as Inhibitors of Dipeptidyl Peptidase IV (CD26), *Tetrahedron,* (1995), 52:291–304.

Duke–Cohan, J.S., et al., "Targeting of an Activated T–Cell Subset Using a Bispecific Antibody–Toxin ConjugatedDirected Against CD4 and CD26", *Blood,* (1993), 82:2224–2234, (Abstract).

Kameoka, J., et al., "Direct Association of Adenosine Deaminase with a T Cell Activation Antigen, CD26", *Science,* 261:466–469. (Abstract).

Hegen, M., et al., "Function of Dipeptidyl Peptidase IV (CD26, TP103) in Transfected Human T Cells", *Cell Immunol,* (1993), 146:249–260. (Abstract).

Hegen, M., et al., "Enzymatic Activity of CD26 (Dipeptidase IV) is not Required for its Signalling Function in T Cells", *Immunobiology,* (1993), 189:483–493. (Abstract).

Tanaka, T., et al., "The Costimulatory Activity of the CD26 Antigen Requires Dipeptidyl Peptidase IV Enzymatic Activity", *Proc Natl Acad Sci U S A,* (1993), 90:4586–4590. (Abstract).

Tanaka, T., et al., "Cloning and Functional Expression of the T Cell Activation Antigen CD26", *J Immunol,* (1992), 149:481–486. (Abstract).

Scharpe, S., et al., "Purified and Cell–Bound CD26: Enzymatic Inhibition, Antibody Binding Profile, and Expression on T Cells in Relation to Other Surface Markers", *Verh K Acad Geneeskd Belg,* (1994), 56:537–559. (Abstract).

Kameoka, J., et al., "Differential CD26–Mediated Activation of the CD3 and CD2 Pathways After CD6–Depleted Allogeneic Bone Marrow Transplantation", *Blood,* (1995), 85:1132–1137. (Abstract).

Mittrucker, H.W., et al., "The Cytoplasmic Tail of the T Cell Receptor Zeta Chain is Required for Signaling Via CD26", *Eur J Immunol,* (1995), 25:295–297. (Abstract).

Morimoto, C., et al., 1F7 "A Novel Cell Surface Molecule, Involved In Helper Function Of CD4 cells", *J Of Im Immunol.* 143:34030–3439 (1989) and published erratum appears in *J Immunology* 144 (5):2027 (Mar. 1990). Abstract.

Barton, R.W.J., et al., "Binding Of The T Cell Activation Monoclonal Antibody Ta1 To Dipeptidyl Peptidase IV", *J. Of Leukocyte Biology* 48:291–296 (1990). Abstract.

Bristol, L.A., et al., "Thymocyte Costimulation Antigen is CD26 (Dipeptidyl–Peptidase IV), Co–stimulation Of Granulocyte, Macrophage, T Lineage Cell Proliferation Via CD26," *J. Of Immunol.* 149:367–372 (1992). Abstract.

Bristol, L.A., et al., "Characterization Of A Novel Rat Thymocyte Costimulating Antigen By The Monoclonal Monoclonal Antibody 1.3", *J. Of Immunol.* 148:332–338 (1992). Abstract.

Fleisher, B., et al., "Triggering Of Cytotoxic T Lymphocytes And NK Cells Via The Tp103 Pathway is Dependent On the Expression Of The T Cell Receptor/CD3 Complex", *J. Of Immunol.* 141:1103–1107 Abstract.

Hegen, M., et al., "The T Cell Triggering Molecule TP103. . . " *J. Immunol.* 144:2980–2914 (1990). Abstract.

Darmoul, D., et al., "Dipeptidyl Peptidase IV (CD26) Gene Expression In Enterocyte–like Colon Cancer Cell Lines HT–29 And Caco–2: Cloning Of The Complete Human Coding Sequence And Changes Of Dipeptidyl Peptidase IV mRNA Levels During Cell Differentiation," *J. Of Biological Chemistry* 267:220–2208 (1992).

Tanaka, T., et al., "Cloning And Functional Expression Of The Cell Activation Antigen CD26" *J. Of Immunol Immunol.* 149:481–486 (1992); published erratum appears in *J. Immunol.* 50(5): 2090 (Mar. 1993). Abstract.

Heins, J., et al., "Mechanism Of Proline–Specific Proteinases: (I) Substrate Specificity of Dipeptidyl Peptidase IV From Pig Kidney And Proline–Specific Endopeptidase From *Flavobacterium Meningosepticum", Biochimica Et Biophysica Acta* 954:161–169 (1988). Abstract.

Schon, E., et al., "Dipeptidyl Peptidase IV In The Immune System. Effects of Specific Enzyme Inhibitors On On Activity Of Dipeptidyl Peptidase IV And Proliferation Of Human Lymphocytes", *Biological Chemistry* Hoppe Seyler 372:305–311 (1991). Abstract.

Schon, E. et al., "The Dipeptidyl Peptidase IV, A Membrane Enzyme Involved In The Proliferation . . . Lymphocytes", *Biomedica Biochimica Acta* 44 (1985). Abstract.

Schon, E., et al., "Dipeptidyl Peptidase IV In Human T Lymphocytes. An Approach To The Role Of A Membrane Peptidase In The Immune System", *Biomedica Biochimica Acta* 45:1523–1528 (1986) Abstract. Abstract.

Schon, E., et al., "The Role Of Dipeptidyl Peptidase IV In Human T Lymphocyte Activation. Inhibitors And Antibodies Against Dipeptidyl Peptidase IV Suppress Lymphocyte Proliferation And Immunoglobulin Synthesis In Vitro", *Eur. J. Of Immunol.* 17:1821–1826 (1987). Abstract.

Freeman, et al., *"Clinical & Experimental Immunology"* 88(2): 275–279 (May 1992). Abstract.

Perry, et al., *Eur. J. Of Immunol.* 26(1): 136–141 (Jan. 1996). Abstract.

Goodstone, et al., *Annals Of The Rheumatic Diseases* 55(1):40–46 (Jan. 1996). Abstract.

Hall, et al., *Seminars in Dermatology,* 10(3):240–245 (Sep. 1991). Abstract.

Karges et al., *Molecular Aspects Of Medicine* 16(2):29–213 (1995). Abstract.

Brenchley, et al., *Nephrology, Dialysis, Transplantation* 7 Supp.1:121 (1992). Abstract.

Kalluri, et al., *J. Of The American Society Of Nephrology* 6 (4):1178–1185 (Oct. 1995). Abstract.

Mullins et al., *J. Of Clinical Investigation* 96 (1):30–37 (Jul. 1996). Abstract.

El Far, et al., *J. Of Neurochemistry*, 64 (4): 1696–1702 (Apr. 1995). Abstract.

James, et al., *Clinical & Experimental Rheumatology*, 13 (3):299–305 (May–Jun. (1995). Abstract.

Van Noort, et al., *Nature* 375 (6534):798–801 (Jun. 29, 1995). Abstract.

Protti, et al., *Immunol. Today* 14 (7): 363–368 (Jul. 1993). Abstract.

Linington, et al., *Eur. J. Of Immunol.* 22 (7): 1813–1817 (Jul. 1992). Abstract.

Chan, et al., *Archives Of Ophthalmology* 113 (5): 597–600 (May 1995). Abstract.

Liu, et al., *J. Of Immunol.* 155(11): 5449–5454 (Dec. 1995). Abstract.

Uibo, et al., *J. Of Autoimmunity* 7 (3): 399–411 (Jun. 1994). Abstract.

Kokawa, et al., *Eur. J. Of Hematology* 50 (2): 74–80 (1993). Abstract.

Daw, et al., *J. Of Immunol.* 156 (2): 818–825 (Jan. 15, 1996). Abstract.

Chazenblak, et al., *J. Of Clinical Investigation* 92 (1):62–74 (Jul. 1993). Abstract.

Hart, et al., *Pharmaceutical Biotechnology* 6:821–845 (1995). Abstract.

Lopez, et al., *Vaccine* 12 (7):585–591 (1994). Abstract.

Reynolds, et al., *J. Of Immunol.* 152 (1):193–200 (Jan. 1, 1994). Abstract.

Nardelli, et al., *J. Of Immunol.* 148 (3):914–920 (Feb. 1, 1992). Abstract.

Darcy, et al., *J. of Immunol.* 149 (11): 3636–3641 (Dec. 1, 1992). Abstract.

Ritu, et al., *Vaccine* 10 (11): 761–765 (1992). Abstract.

Ikagawa, et al., *J. Of Allergy & Clinical Immunol.* 97 (1 Pt. 1): 53–64 (Jan. 1996). Abstract.

Brander, et al., *J. Of Immunol.* 155 (5):2670–2678 (Sep. 1, 1995). Abstract.

O'Brien, et al., *Immunology* 86 (2):176–182 (Oct. 1995). Abstract.

Zhu, X., et al., *J. Of Immunol.* 155 (10):5064–5073 (Nov. 15, 1995). Abstract.

Dudler, et al., *Eur. J. Of Immunol.* 25 (2):538–542 (Feb. 1995). Abstract.

Bungy, et al., *Eur. J. Of Immunol.* 24 (9):2098–2103 (Sep. 1994). Abstract.

Shimojo, et al., *Int'l. Archives Of Allergy & Immunol.* 105 (2):155–161 (Oct. 1994). Abstract.

Kelly, T.A., et al., "The Efficient Synthesis And Simple Resolution Of A Proline Boronate Ester Suitable For Enzyme Inhibition Studies", *Tetrahedron* 49:1009–1016 (1993). Abstract.

Watson, J.D., "Continuous Proliferation Of Murine Antigen Specific Helper T Lymphocytes In Culture", *J. Of Experimental Medicine* 150:1510 (1979). Abstract.

Kuchroo, V.K., et al., "Induction Of Experimental Allergic Encephalomyelitis By Myelin Proteolipid–Protein–Specific T Cell Clones And Synthetic Peptides", *Pathology* 59:305–312 (1991). Abstract.

Kuchroo, V.K., et al.,"T–cell Receptor Alpha Chain Plays A Critical Role In Antigen–Specific Suppressor Cell Function", *Proceedings Of The Nat'l. Academy Of Sciences Of The United States Of America* 88:8700 88:8700–8704 (1991). Abstract.

Kuchroo, V.K., et al., "Experimental Allergic Encephalomyelitis Medicated By Cloned T Cells Specific For A Synthetic Peptide of Myelin Proteolipid Protein. Fine Specificity And T Cell Receptor V Beta Usage", *J. Of Immunol.* 148:3776–3782 (1992). Abstract.

Kuchroo, V.K., et al., "Cytokines And Adhesion Molecules Contribute To The Ability Of Myelin Proteolipid Protein- -Specific T Cell Clones To Mediate Experimental Allergic Encephalomyelitis", *J. Of Immunol.* 151:4371–4382 (1993). Abstract.

Kuchroo, V.K., et al., "T Cell Receptor (TCR) Usage Determines Disease Susceptibility in Experimental Autoimmune Encephalomyelitis: Studies with TCR V Beta *.2 Tranagenic Mice", *J. Of Experimental Medicine* 179:1659–1664 (1994). Abstract.

Kuchroo, V.K. et al., "A Single TCR Antagonist Peptide Inhibits Experimental Allergic Encnephalomyelitis Mediated By A Diverse T Cell Repertoire", *J. Of Immunol.*, 153:3326–3336 (1994). Abstract.

Jorgensen, J.L., et al., "Molecular Components Of T–Cell Recognition," *Annu. Rev. Immunol.* 10:835–873 (1992). Abstract.

Wyse–Coray, T., et al., "Use Of Antibody/Peptides Constructs Of Direct Antigenic Peptides To T Cells: Evidence For T Cells Processing And Presentation", *Cellular Immunol.*, 139 (1):268–73 (1992). Abstract.

Panina–Bordignon, P., et al., "Universally Immunogenic T Cell Epitopes: Promiscuous Binding To Human MHC MHC Class II and Promiscuous Recognition By T Cells", *Eur. J. Immunl.* 19:2237–2242 (1989). Abstract.

Ebenbichler, C.,. et al., "Structure–function Relationships Of The HIV–1 Envelope V3 Loop Tropism Determinant: Evidence For Two Distinct Conformations", *Aids* 7:639–46 (1993). Abstract.

Linsley, P.S., et al., "Effects Of Anti–gp120 Monoclonal Antibodies On CD4 Receptor Binding By The Env Protein Of Human Immunodeficiency Virus Type 1", *J. Of Virology* 62:3695–3702 (1988). Abstract.

Rini, J.M., et al., "Crystal Structure Of A Human Immunodeficiency Virus Type 1 Neutralizing Antibody, 50.1, In Complex With Its V3 Loop Peptide Antigen", *Proceedings Of The Nat'l Academy Of Sciences Of The United States Of America* 90:6325–9 (1993). Abstract.

Subramanyam, W.G., et al., "Mechanism Of HIV–1 TAT Induced Inhibition Of Antigen–Specific T Cell Responsiveness", *J. Of Immunol.* 150:2544–2553 (1993). Abstract.

Dang, N.H., et al., "Cell Surface Modulation Of CD26 By Anti–1F7 Monoclonal Antibody: Analysis Of Surface Expression And Human T Cell Activation", *J. Of Immunol.* 145:3963–3971 (1990). Abstract.

De Caestecker, M.P., et al., "The Detection Of Intercytoplasmic Interleukin 1 (Alpha) Expression in Human Monocytes Using Two Colour Immunofluorescence Flow Cytometry", *J. Immunol. Methods* 154:11–20 (1992). Abstract.

Fauci, A.S., "The Human Immunodeficiency Virus: Infectivity And Mechanisms Of Pathogenesis", *Science* 239:617–722 (1988). Abstract.

Kinder, D., et al., "Analogues Of Carbamyl Aspartate as Inhibitors . . . " *J. Med. Chem.*, (1990), 33:819–823.

Snow, R., et al., "Studies on Proline Boronic Acid Dipeptide Inhibityors of Dipeptidyl . . . " *J. Med. Chem,* (1990). 116:10860–10869.

TREATMENT OF HIV

This application is a continuation of U.S. Ser. No. 08/852,394 filed on May 7, 1997 now U.S. Pat. No. 6,100,234.

STATEMENT AS TO FEDERALLY SPONSORED RESEARCH

This invention was made with Government support under NIH grant No. AI36696, and the Government therefore has certain rights in this invention.

BACKGROUND OF THE INVENTION

This invention relates to treatment of HIV.

One of the classic markers of full-blown AIDS resulting from long-term infection with HIV-1 is a severe depletion of CD4+ T-cells, which are a key component of the immune system. Attempts have been made to increase the CD4+ counts of AIDS patients, and some of these efforts, notably treatment with HIV protease inhibitors, have met with considerable success. Other approaches, e.g., stimulation of the immune response by vaccination with viral peptides, have been less successful. The reasons for CD4+ depletion in AIDS, and resistance of CD4+ cells to stimulation by some therapies, are not fully understood.

SUMMARY OF THE INVENTION

The invention provides a new and highly advantageous method of potentiating the immune response in HIV-infected patients, employing extremely low concentrations of compounds which, at these concentrations, act as stimulatory, rather than inhibitory, molecules. The very low concentrations employed according to the invention allow treatment with minimal side effects and toxicity. The specificity of the treatments according to the invention also helps avoid these adverse effects, which are seen, for example, in treatment with immune stimulatory compounds such as Interleukin-2.

The invention involves the unexpected finding that certain compounds, which at relatively low concentrations (e.g. $10^{-4}$–$10^{-6}$) are cytotoxic to T-cells, nevertheless have immune stimulatory properties at extremely low concentrations (e.g. $10^{-10}$–$10^{14}$). Even more surprising, this stimulation occurs even though the HIV-infected patient's T-cells are otherwise unable to respond to T-cell proliferation-inducing stimuli. The effects of these low concentrations are paraxodical because T-cells from non-HIV-infected individuals, which respond to T-cell proliferation-inducing stimuli, do not seem to respond in the same fashion as T-cells from an HIV-infected patient when treated with the extremely low concentrations of compounds according to the invention.

The invention thus provides a method for treating the T-cells of a human subject infected with human immunodeficiency virus. The subject's T-cells are contacted with a molecule that inhibits CD26 and that stimulates immune function of the T-cells in an amount effective to stimulate immune function of the T-cells, said amount being below a concentration which causes detectable cytotoxicity of the T-cells. In one embodiment, the molecule stimulates proliferation of T-cells at the effective concentration. In other embodiments, the molecule stimulates the production of cytokines or increases cytotoxic T-lymphocyte or antibody activity.

The T-cells can be contacted in vitro or in vivo. In certain embodiments, the effective amount is below $10^{-8}$M and may be between $10^{-10}$ and $10^{-16}$ M. Molarity is measured as a function of final concentration in vitro and as a function of blood concentration in vivo.

According to another aspect of the invention, the molecule can be administered in conjunction with a different therapeutic agent that increases the CD4+ count of HIV-infected subjects. In this manner, treatment with effective amounts of the molecule according to the invention can enhance the therapeutic effect of other AIDS drugs. Specifically contemplated is use of the molecules according to the invention with non CD26 protease inhibitors. It has been determined that the effects of the treatments according to the invention are particularly good in patients whose CD4+ count is above about 400. In one embodiment, subjects may be treated with therapeutic agents or regimens to increase T-cell count to above 400 where the count initially is below 400. The subjects then are believed to be better candidates for treatment according to the invention. Thus, the invention contemplates the use of the molecules according to the invention to provide optimal combination AIDS therapies. Particularly contemplated for use in conjunction with the molecules of the invention are therapeutics which inhibit HIV replication by, for example, inhibiting reverse transcriptase or by inhibiting HIV protease activity. Exemplary therapeutics include the antiretroviral drugs: AZT (3' azido-2',3' dideoxythymidine), ddI (2',3' dideoxyinosine), (2',3' dideoxycytidine), ddt (2',3' didehydro-3'-deoxythymidine) and other nucleoside and non-nucleoside reverse transcriptase inhibitors and HIV-1 protease inhibitors: Indinavir, Ritonavir, Saquinavir. Combination therapies include the administration of one or more of these or other antiretroviral therapeutics, alone or together with therapeutics that are intended to treat the secondary infections associated with HIV and/or cytokines (e.g., GM-CSF, G-CSF, interferons, interleukins)

According to another aspect of the invention, the molecules of the invention are contacted with T-cells of a human subject infected with HIV, which T-cells are unable, prior to treatment according to the invention to respond normally to T-cell proliferation-inducing stimuli. In one particularly important embodiment, the molecules of the invention are administered in conjunction with an antigen. Ordinarily, such HIV-infected patients do not respond well to antigens because of an HIV-induced defect in the T-cell stimulation pathway. Use of the molecules according to the invention as adjuvants can render such T-cells responsive to stimulation or vaccination with antigens. The invention permits immunization of HIV-infected patients with antigens characteristic of HIV, antigens characteristic of other pathogens, antigens characteristic of cancer cells and the like. Peptide antigens in particular are contemplated.

Compounds useful in the invention inhibit CD26 and stimulate proliferation of T-cells of HIV-infected subjects in the assays and at the concentrations described below. CD26 is also referred to as "dipeptidyl-aminopeptidase type-IV" or "DP-IV". CD26 is a post-prolyl cleaving enzyme with a specificity for removing Xaa-Pro (where Xaa represents any amino acid) dipeptides from the amino terminus of a polypeptide substrate.

Peptides which reportedly have demonstrated utility for inhibiting post-prolyl cleaving enzymes and which, if coupled to a reactive group, form a covalent complex with a functional group in the reactive site of a post-prolyl cleaving enzyme are described in U.S. Pat. No. 4,935,493, "Protease Inhibitors", issued to Bachovchin et al. ("Bachovchin '493"); U.S. Pat. No. 5,462,928, "Inhibitors of Dipeptidyl-aminopeptidase Type IV", issued to Bachovchin et al. ("Bachovchin '928"); U.S. Pat. No. 5,543,396, "Proline Phosphonate Derivatives", issued to Powers et al., ("Powers '396"); U.S. Pat. No. 5,296,604, "Proline Derivatives and Compositions for Their Use as Inhibitors of HIV Protease", issued to Hanko et al., ("Hanko '604"); PCT/US92/09845, "Method for Making a Prolineboronate Ester", and its U.S. priority applications (U.S. Ser. Nos. 07/796,148 and 07/936,198), Applicant Boehringer Ingelheim Pharmaceuticals, Inc. ("Boehringer"). Representative structures of the transition-state analog-based inhibitors Xaa-Boo-Pro, include Lys-boroPro, Pro-boroPro, Val-boroPro and Ala-boroPro in which "boroPro" refers to the analog of proline in which the carboxylate group (COOH) is replaced with a boronyl group (B) (OH$_2$).

In general, the molecules useful according to the invention can have a first targeting moiety for binding a post-prolyl cleaving enzyme such as CD26 covalently coupled to a first reactive group. As used herein, a reactive group is capable of reacting with a functional group in a post-prolyl cleaving enzyme such as CD26. By reacting, it is meant that the reactive group forms a bond with a functional group of a post-prolyl cleaving enzyme such as CD26. Reactive groups that are embraced within the invention include the reactive groups referred to as group "T" in U.S. Pat. No. 4,935,493, "Protease Inhibitors", issued to Bachovchin, et al. These include boronate groups, phosphonate groups, and fluoroalkylketone groups. In general, it is preferred that the linkage between the carboxyl terminus of preferred peptide targeting moieties and the reactive group be in an L configuration. It is preferred that the reactive group form a covalent bond with a functional group of the active site of a reactive center of CD26; however, there is no requirement for covalent bond formation in order to form a complex between the CD26 binding molecule and CD26.

The reactive groups that are fluoroalkylketone groups have the formula:

where G is either H, F or an alkyl group containing 1 to about 20 carbon atoms and optional heteroatoms which can be N, S, or O. Additional exemplary proline phosphonate derivatives which contain a perfluoroalkyl group, a phenyl group or a substituted phenyl group and which can be used in accordance with the methods of the invention are those described in U.S. Pat. No. 5,543,396 (Powers '396).

The reactive groups that are phosphonate groups have the formula:

where each J, independently, is O-alkyl, N-alkyl, or alkyl (each containing about 1–20 carbon atoms) and, optionally, heteroatoms which can be n=N, S, or O. Other ketoamides, ketoacids and ketoesters that are useful reactive groups for reacting with the reactive center of a protease are described in PCT/US91/09801, "Peptides, Ketoamides, Ketoacids, and Ketoesters", Applicant: Georgia Tech Research Corp. ("GA Tech") which claims priority to U.S. Pat. No. 635,287, filed Dec. 28, 1990.

In certain embodiments, the reactive groups are selected from the groups having the formulas an alphaketo amide;

where R is an alkyl, or aryl group and may be substituted or unsubstituted, an alphaketo ester; and an alphaketo acid.

The preferred compounds have targeting moieties that are peptides which mimic the substrate binding site of DP-IV. Peptide analogs and nonpeptides or peptidomimetics also can be used as targeting moieties. Such molecules can be rationally designed based upon the known sequence of substrates of DP-IV or can be identified using combinatorial chemistry and screening assays such as are described below.

The development of phage display libraries and chemical combinatorial libraries permits the selection of synthetic compounds which mimic the substrate binding site of a protease such as CD26. Such libraries can be screened to identify non-naturally occurring putative targeting moieties by assaying protease cleavage activity in the presence and absence of the putative phage display library molecule or combinatorial library molecule and determining whether the molecule inhibits cleavage by the protease of its natural substrate or of a substrate analog (e.g., a chromophoric substrate analog which is easily detectable in a spectrophotometric assay). Those phage library and/or combinatorial library molecules which exhibit inhibition of the protease then can be covalently coupled to the reactive groups R disclosed herein and again tested to determine whether these novel molecules selectively bind to the protease (e.g., by repeating the above-noted screening assay). In this manner, a simple, high-through-put screening assay is provided for identifying non-naturally occurring targeting moieties of the invention.

Compounds useful in the invention include, but are not limited to, compounds that inhibit CD26 and are embraced by the following formula PR, wherein P represents a targeting moiety that binds to CD26 and R represents a reactive group that reacts with a functional group in CD26, preferably a reactive center of CD26. P can be any molecule that binds CD26 including CD26 binding molecules embraced by the formula: D—A$_1$—A$_2$—A$_3$—A$_4$, wherein D is independently selected from the group consisting of NH and NH$_2$, wherein N represents any isotope of nitrogen, herein H represents any isotope of hydrogen; "—", independently, is selected from the group consisting of a single bond and a double bond; A$_1$ is selected from the group consisting of a C, a CX and an N, wherein C represents any isotope of carbon, X represents any atom that forms a single band with carbon; each A$_2$, A$_3$, and A$_4$, independently, is selected from the group consisting of a CX moiety, a CXZ moiety, a CZ moiety, an NX moiety, and an O, wherein X and Z, independently are selected from the group consisting of any atom that forms a single bond and any atom that forms a double bond with C or N and wherein O represent any isotope of oxygen.

Compounds useful according to the invention also include the following of Group I or Group II. Group I has the structure:

where H represents a hydrogen: C represents a carbon; O represents an oxygen; N represents a nitrogen; each R, independently, is chosen from the group consisting of the R groups of an amino acid, including proline; each broken line, independently, represents a bond to an H or a bond to one R group, and each H' represents that bond or a hydrogen; and p is an integer between 0 and 4 inclusive. Alternatively, Group I has the structure:

where n is between 0 and 3 inclusive, each G2 and G3 independently is H or C1–3 (one to three carbon atoms) alkyl, G1 is NH3 (H3 represents three hydrogens),

(H2 represents two hydrogens), or NG4, where G4 is where G5 and G6 can be NH, H, or C1–3 alkyl or alkenyl with one or more carbons substituted with a nitrogen. G1 bears a charged, and G1 and Group II do not form a covalently bonded ring structure at pH 7.0. Group I may also have the structure:

where one or two of the a, b, c, d, e, and f group is N. and the rest are C, and each S1–S6 independently is H or C1–C3 alkyl. Group I may also include a five membered unsaturated ring having two nitrogen atoms, e.g., an imidazole ring. Group II has the structure:

where T is a group of the formula:

where each D1 and D2, independently, is a hydroxyl group or a group which is capable of being hydrolysed to a hydroxyl group in aqueous solution at physiological pH; a group of the formula:

where G is either H, fluorine (F) or an alkyl group containing 1 to 20 carbon atoms and optional heteroatoms which can be N, S (sulfur) or O; or a phosphonate group of the formula:

where each J, independently, is O-alkyl, N-alkyl, or alkyl. Each O-alkyl, N-alkyl or alkyl includes 1–20 carbon atoms and, optionally, heteroatoms which can be N, S, or O. T is generally able to form a complex with the catalytic site of a DP-IV. Y is and each R1, R2, R3, R4, R5, R6, R7, and R8, separately is a group which does not significantly interfere with site specific recognition of the inhibitory compound by DP-IV, and allows a complex to be formed with DP-IV.

In preferred embodiments, T is a boronate group, a phosphonate group or a trifluoroalkyl ketone group; each R1–R8 is H; each R1 and R2 is H, and each Y is the $CH_2$—$CH_2$; each R is independently chosen from the R group of proline and alanine; the inhibitory compound has a binding or dissociation constant to DP-IV of at least $10^{-9}M$, $10^{-8}M$ or even $10^{-7}M$; and each D1 and D2 is, independently, F or D1 and D2 together are a ring containing 1 to 20 carbon atoms, and optionally heteroatoms which can be N, S, or O. These compounds are described in U.S. Pat. No. 5,462,928, hereby incorporated by reference.

More preferably, the compound used at low concentration according to the invention has the formula wherein m is an integer between 0 and 10, inclusive; A and $A^1$ are amino acid residues such that the A in each repeating bracketed unit can be a different amino acid residue; the bonds between A and N, $A^1$ and C, and between $A^1$ and N are peptide bonds; and each $X^1$ and $X^2$ is, independently, a hydroxyl group or a group capable of being hydrolyzed to a hydroxyl group at physiological pH. These compounds are also described in U.S. Pat. No. 5,462,928.

The most preferred compounds are of the formula where each $D^1$ and $D^2$, independently, is a hydroxyl group or a group which is capable of being hydrolyzed to a hydroxyl group in aqueous solution at physiological pH;

and wherein X is a targeting moiety that mimics the site of a substrate recognized and cleaved by CD26.

Other features and advantages of the invention will be apparent from the following detailed description thereof, and from the claims.

DETAILED DESCRIPTION OF THE INVENTION

In general, the compounds useful according to the invention are capable of stimulating immune function of T-cells from HIV-infected human subjects. Stimulation of immune function is preferably determined by measuring whether T-cells proliferate in response to treatment according to the invention. Assays for proliferation are described below. Stimulation of immune function also can be determined by detecting an increase in cytokine release or by detecting an increase in cytotoxic T-lymphocyte or antibody activity, using routine, commercially available assays and/or reagents.

The molecules are contacted with T-cells in amounts effective to stimulate immune function. Effective amounts are those which cause detectable changes in any one or more of the foregoing parameters. Thus, for example, an effective amount can be that amount which induces measurable proliferation of an HIV-infected subject's T-cells. The effective amounts according to the invention, however, are amounts below a concentration which causes detectable cytotoxicity of a patient's T-cells. As used herein, detectable cytotoxicity means no more than 20%, preferably no more than 10% and most preferably no more than 5% cytotoxicity as compared to controls. At such levels, the proliferation effects of the compounds will outweigh the cytotoxic effects.

An important aspect of the invention is the discovery that relatively high concentrations (e.g. $10^{-4}$–$10^{-4}$ Molar) of certain compounds useful according to the invention cause substantial cytotoxicity of T-cells. For example, using Val-boroPro, greater than 80% toxicity was observed in vitro at a concentration of $10^{-4}$M and approximately 50% cytotoxicity was observed at a concentration of $10^{-6}$M. Although cytotoxicity decreased with decreasing concentrations of Val-boroPro, it was not expected that there would be such substantial cytotoxicity at concentrations of $10^{-6}$. Unexpectedly, however, stimulatory properties increased substantially at concentrations significantly below those concentrations which were cytotoxic. Maximum stimulation was observed at concentrations of $10^{-12}$–$10^{-14}$M. Thus, the compounds according to the invention can be applied at extremely low concentrations in vitro, or in vivo, thereby avoiding any detectable cytotoxicity yet achieving the highest levels of immune stimulation.

The foregoing observation is important when considering treatments of T-cells of HIV-infected subjects, particularly in vivo. AIDS subjects already suffer drastic reductions in T-cells. It could be catastrophic to administer compounds which would destroy the relatively meager amount of T-cells present in an AIDS patient. The present invention is based upon the discovery that concentrations of certain compounds can be applied far below those concentrations that would be cytotoxic while achieving the highest levels of immune stimulation capable of being induced by such compounds.

In selecting effective amounts for in vivo treatment, concentrations can be selected far outside the range that would be expected to cause cytotoxicity. This concentration then could be increased, all the while measuring T-cell count, until maximum stimulation is observed (as in a bell curve). Maximum stimulation will occur, as shown in the Examples below, long before cytotoxic levels are achieved. Thus, effective in vivo dosing can be accomplished without risk to the patient. In selecting amounts for in vitro treatment, assays such as those shown in the Examples below can be used. One such assay employs the candidate compound at very low concentrations, in a test designed to determine whether at such concentrations the compound can stimulate proliferation of PBMC from HIV-infected patients in vitro. As is shown in the Examples, stimulation can be measured by, e.g. incorporation of a labeled nucleotide. In vitro screening also can be used to assist in developing in vivo effective amounts.

Where in vitro treatment is contemplated, cells are obtained from a subject, stimulated in vitro, and then returned to the subject in a conventional manner. Where in vivo treatment is contemplated, the compounds useful according to the invention are administered in a conventional manner, as described in greater detail below.

The molecules useful according to the invention can be administered in vivo as concurrent therapy or in combination with other AIDS therapeutics. While not wishing to be bound by any theory of the invention, it is believed that the compounds of the invention will beneficially stimulate proliferation of non-infected T-cells in the HIV-infected patient. The concurrent treatments then can be used to bring about proliferation of non-infected T-cells, which in turn can be stimulated beneficially according to the methods of the present invention. The fact that, in T-cells treated according to the invention in vitro no increase in the level of the HIV protein P24 is observed, may indicate that the T-cells which are infected with HIV are not stimulated by the low dose treatment of the invention. The inventors explicitly, however, do not intend to be bound by this theory of the invention.

Particularly preferred compounds useful according to the invention are described in the Examples below. The invention, however, embraces the specific compounds described above. In order to identify additional compounds useful according to the invention, simple screening assays can be employed. First, compounds rationally designed based upon the natural substrate of a post-prolyl cleaving enzyme or libraries of compounds prepared by combinatorial chemistry or phase display are screened for their ability to inhibit CD26. CD26 and methods of purifying CD26 are well known to those of ordinary skill in the art. Torimoto, Y., et al. Molecular Immunol. 29:183–192 (1992). Assays which measure, for example, the ability of a molecule to interfere with CD26 cleavage of a standard fluorescent-labeled substrate can be employed. Once a candidate compound that inhibits CD26 is identified, then the compound is tested over a wide range of concentrations (e.g. $10^{-4}$–$10^{-16}$) to determine the ability of the compound to stimulate immune function of T-cells from HIV-infected patients. Methods for performing this test are described in the Examples below, which involve measurement of proliferation.

In the screening assays described in the previous paragraph, a reporter substrate such as Ala-Pro-Afc, which contains a proline in the penultimate position, can be employed. Alternatively, a calorimetric assay can be carried out using as a substrate Gly-Pro-PNA. The choice of terminal amino acid is not critical, provided that the substrate contain a free terminal amino group. A fluorescence spectrometer then can be used to measure cleavage of the reporter substrate. Multiple samples can be run, with or without a test compound. The samples are placed in a cuvette, inserted into a fluorescent spectrometer, and enzymatic activity is measured as the accumulation of fluorescence intensity (i.e. substrate cleavage product) over time (e.g. 1 minute). A compound is identified as a good candidate if the accumulative fluorescence is decreased as a result of the presence of the compound.

When methods are carried out in vivo, the effective amount will vary with the particular condition being treated, the age and physical condition of the subject being treated, the severity of the condition, the duration of the treatment, the nature of the concurrent therapy (if any), the specific route of administration and the like factors within the knowledge and expertise of the health practitioner. For example, an effective amount can depend upon the degree to which an individual has abnormally depressed levels of T cells.

Generally, doses of active compounds would be from about 0.001 mg/kg per a day to 1000 mg/kg per day. It is expected that doses ranging from 0.01–10 mg/kg will be suitable, preferably orally and in one or several administrations per day. Lower doses will result from other forms of administration, such as intravenous administration. In the event that a response in a subject is insufficient at the initial a doses applied, higher doses (or effectively higher doses by a different, more localized delivery route) may be employed to the extent that patient tolerance permits, provided that toxic levels are not administered. Multiple doses per day are contemplated to achieve appropriate systemic levels of compounds.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The molecules may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the anti-inflammatory agent, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active agent into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the active agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di-and triglycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

Certain families of molecules useful according to the invention are described in U.S. Pat. Nos. 4,935,493, 5,462,928, and in U.S. application Ser. No. 07/923,337, corresponding to PCT Application No. WO94/03055. One of the families of molecules described in these patents may be referred to as the Xaa-Boro-Pro molecules, exemplified by Ala-boroPro, Pro-boroPro, and Gly-boroPro. Two of these compounds, used in the Examples described below, are Lys-Boro-Pro ("KPB") and Val-Boro-Pro ("VBP").

EXAMPLES

Peripheral blood mononuclear cells (PBMC) were obtained by standard methods from HIV-infected individuals, and from uninfected individuals. Varying dosages of KBP or VBP were contacted with the PBMC in vitro, and stimulation of proliferation was measured by incorporation of $^3$H thymidine (cpm). The results of these experiments are shown in FIG. 1: very low doses of the Val-Boro-Pro and Lys-Boro-Pro stimulated proliferation of PBMC from HIV-infected patients, but not PBMC from uninfected patients.

Figure 1A:
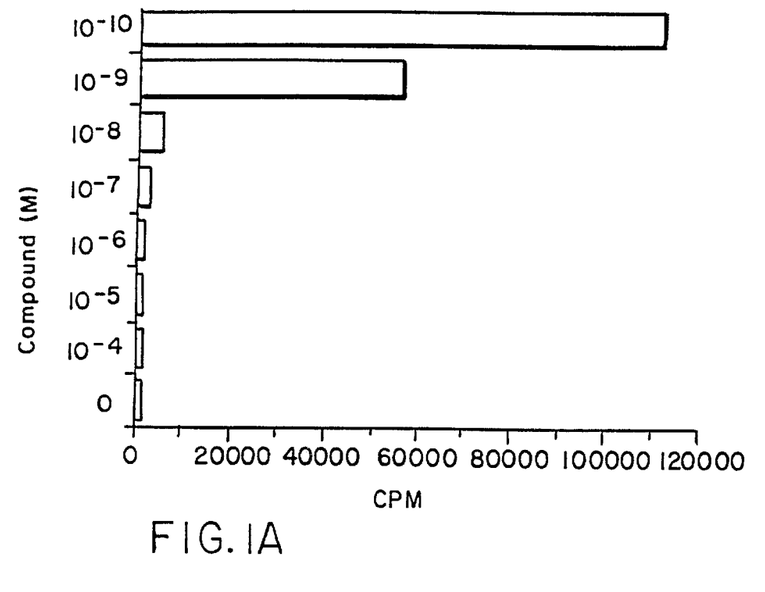
FIG. 1 is a pair of graphs showing the T cell stimulatory effect on lymphocytes from HIV-infected and uninfected patients by a CD26 inhibitor according to the invention.
Figure 1B:
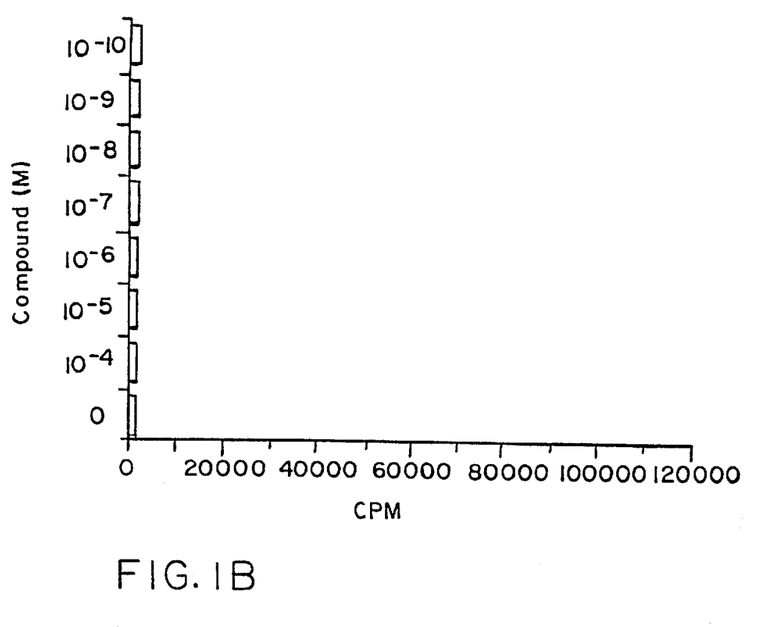
Figure 5:
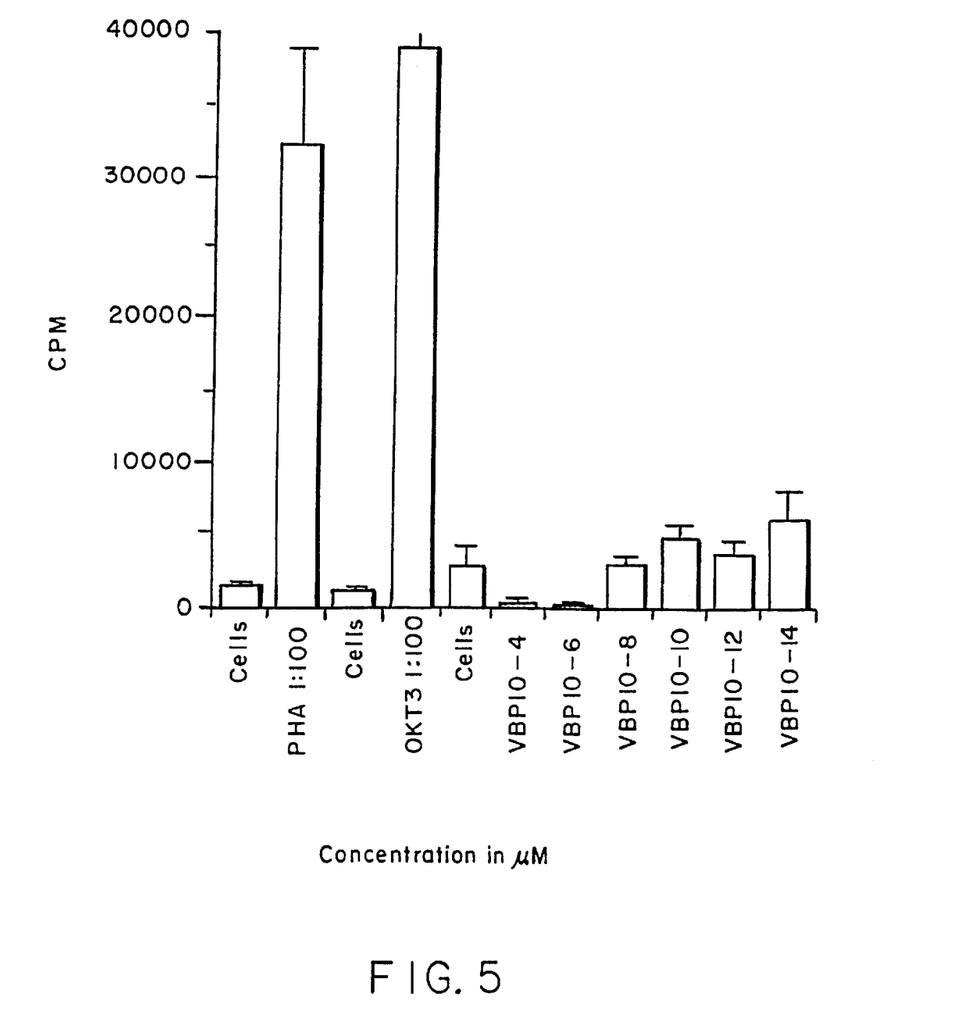
FIGS. 5 and 6 are graphs showing the T cell stimulatory effect on lymphocytes from HIV-infected patients by a CD26 inhibitor according to the invention, and giving results for control compounds.
Figure 6:
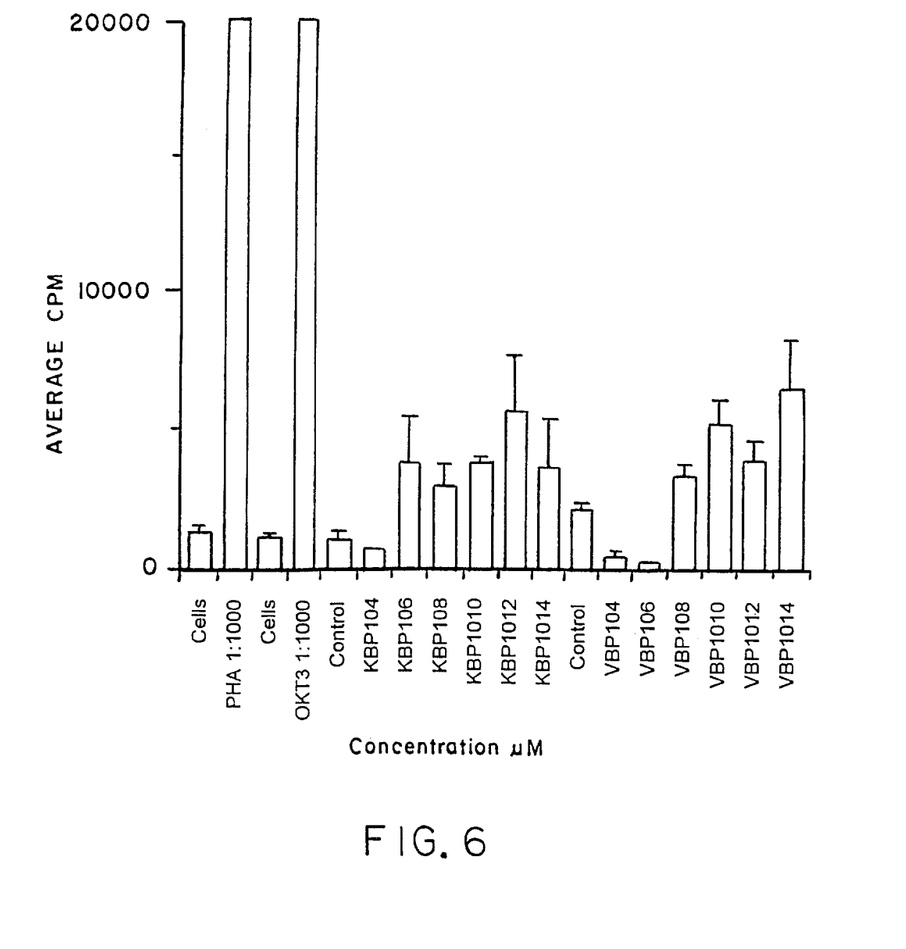

As shown in FIG. 1, at no concentration tested of the compounds did they affect the PBMC from uninfected individuals. The compounds, at moderate concentrations, also did not cause proliferation of PBMC from HIV-infected individuals, but did cause marked proliferation at very low concentrations ($10^{-9}$ and $10^{-10}$). The same results are shown in FIGS. 5 and 6 which also present data for two control compounds OKT3 and PHA, both of which are non-specific mitogens.

Figure 2:
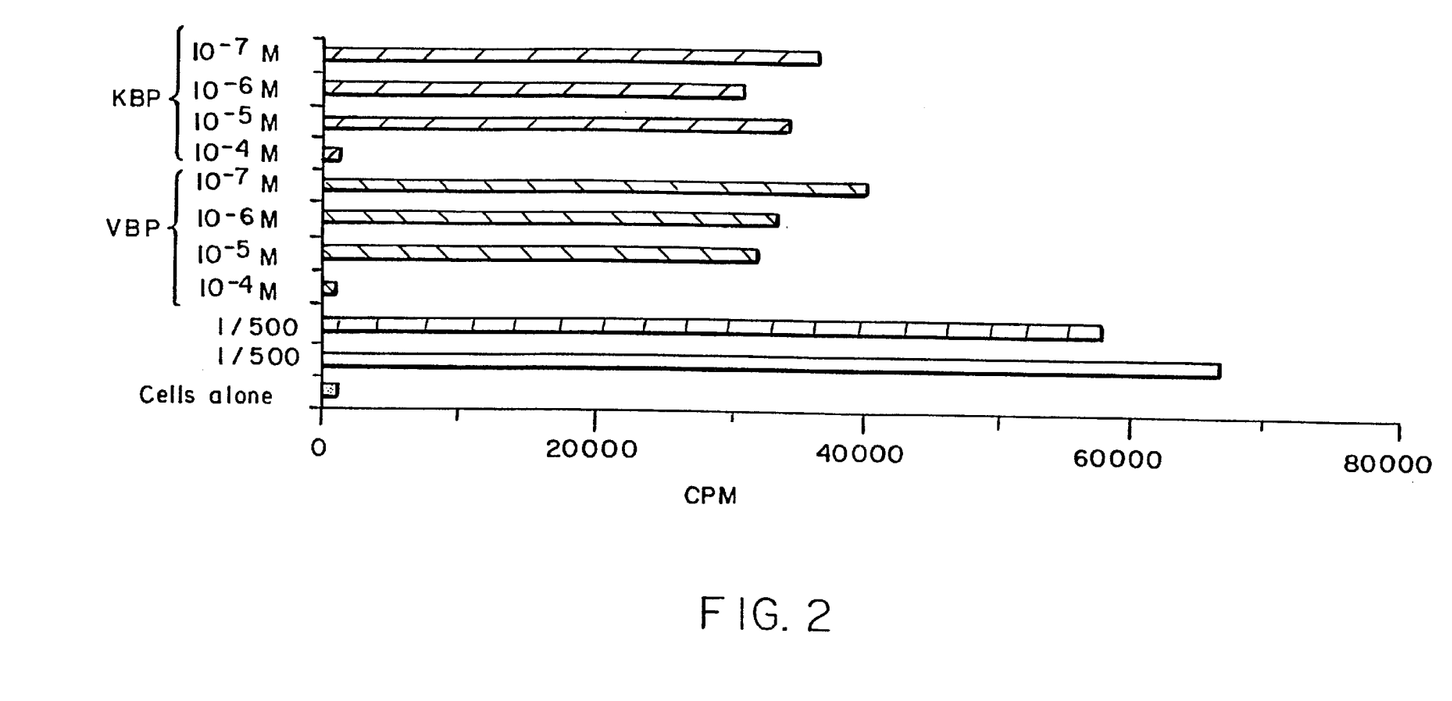
FIG. 2 is a graph showing the T cell stimulatory effects on lymphocytes of HIV-infected patients by two CD26 inhibitors.
Figure 3:
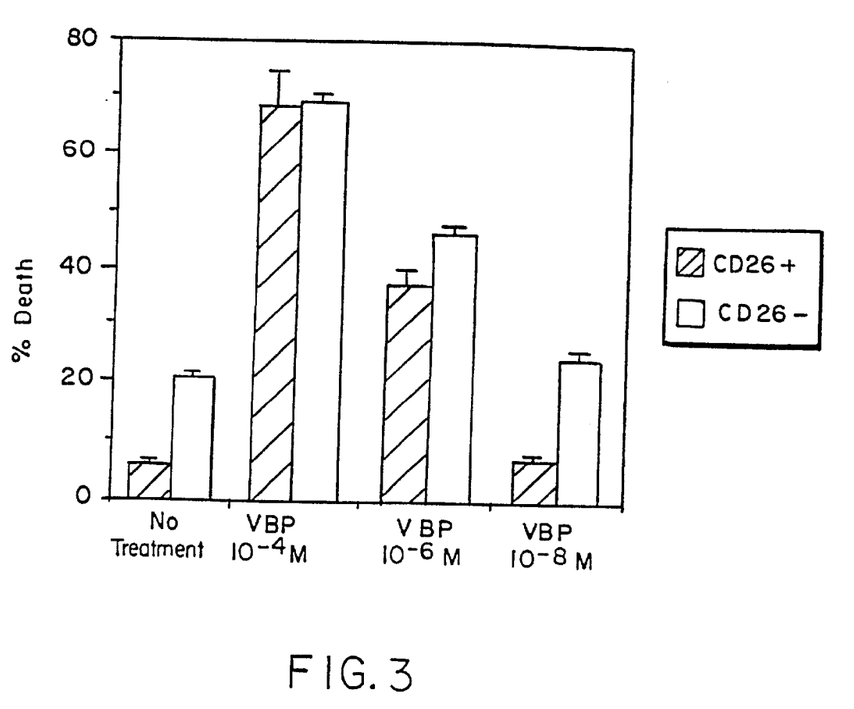
FIG. 3 is a graph showing that T cells are extremely sensitive to CD-26 inhibitor-induced death.

FIG. 2 is a histogram showing that relatively low doses of Lys-boroPro and Val-boroPro ($10^{-7}$M) caused proliferation of PBMC of HIV-infected patients, while higher doses ($10^{-4}$M) did not have this effect. This is to be contrasted with FIG. 3 which shows that Val-boroPro is highly cytotoxic to T-cells at concentrations of $10^{-4}$ and $10^{-6}$. Thus, even though there was stimulation at concentrations of $10^{-6}$ as shown in FIG. 2, it would be undesirable to use Val-boroPro in this range because it would cause T-cell death in patients already severely compromised with T-cell loss. As shown in FIGS. 5 and 6, Val-boroPro can be used successfully outside of this cytotoxic range, avoiding the cytotoxic effects.

Figure 4:
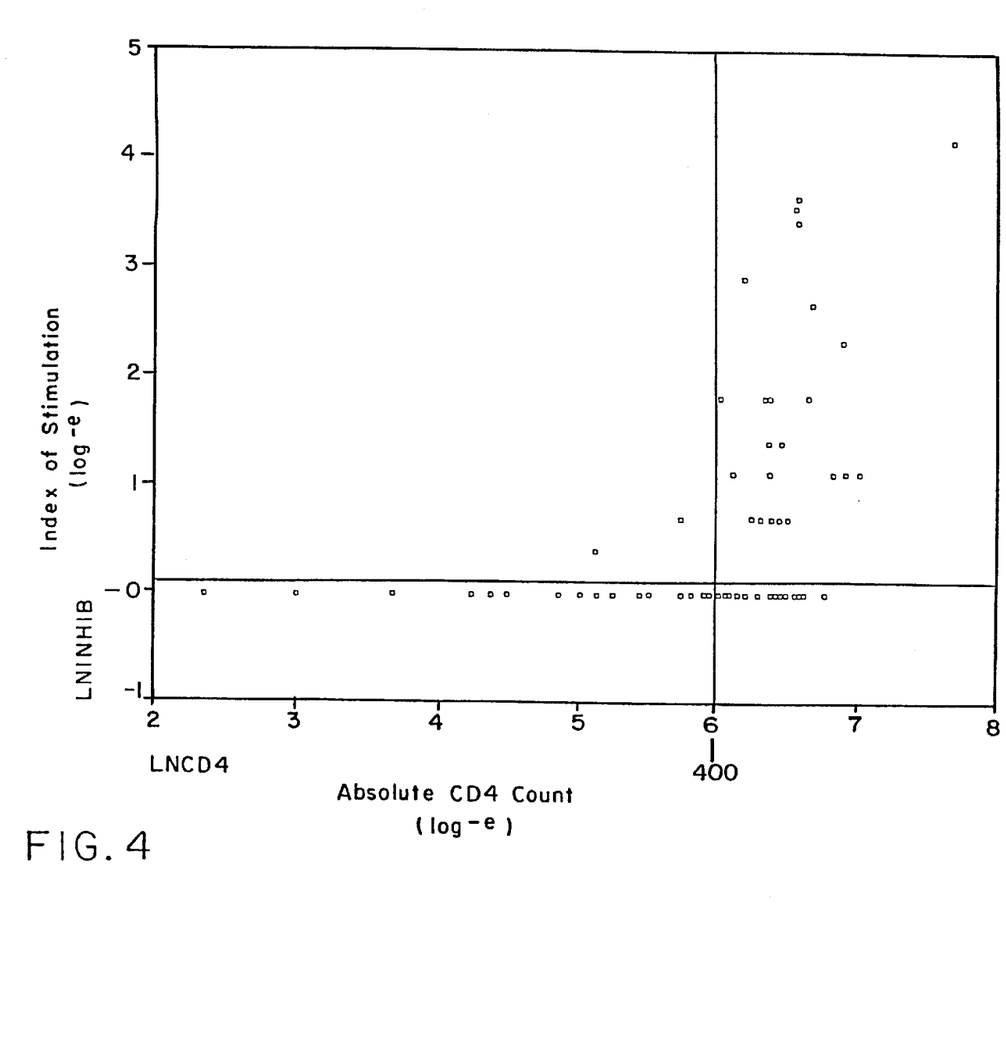
FIG. 4 is a graph showing the T cell stimulatory effect on lymphocytes from HIV-infected patients by CD26 inhibitors, showing the correlation with $CD4^+$ counts. The data are plotted as the natural log of the stimulation index (vertical dimension) versus the natural log of the $CD4^+$ count of the patient (horizontal dimension).

Referring to FIG. 4, data are presented in a form showing that low concentrations of the compounds of the invention have less effect on the PBMC of HIV-infected patients whose CD4$^+$ counts are lower than about 400 (the clinical indication for AIDS) than on the PBMC of HIV-infected patients whose CD4$^+$ counts are higher than about 400. In the graph of FIG. 5, the natural log of the stimulation index (the vertical axis) is plotted against the natural log of the CD4$^+$ count of the patients; as is shown.

The disclosures of any patents and patent applications referenced to herein are expressly incorporated by reference.

We claim:

1. A method for treating the T-cells of a human subject infected with Human Immunodeficiency Virus, comprising contacting said T-cells with a molecule in an amount effective to stimulate immune function of the T-cells, said amount being below a concentration which causes detectable cytotoxicity of said T-cells, said molecule having the formula:

wherein Y is a group of the formula:

and each R1, R2, R3, R4, R5, R6, R7, and R8 is, independently, a group which does not significantly interfere with site specific recognition by DP-IV;

wherein X comprises an amino acid or a peptide that mimics the site of a substrate recognized and cleaved by CD26; and wherein T is a group of the formula:

wherein B is boron, and each $D_1$ and $D_2$ is, independently, a hydroxyl group or a group capable of being hydrolyzed to a hydroxyl group at physiological pH;

a group of the formula:

wherein G is either H, fluorine (F), or an alkyl group containing 1 to 20 carbon atoms and optional heteroatoms which can be N, S, or O;

a group of the formula:

a group of the formula:

wherein R is a substituted or unsubstituted alkyl or aryl group; or a group of the formula:

2. The method of claim 1, wherein said molecule stimulates proliferation of said T-cells at said effective concentration.

3. The method of claim 1, wherein the T-cells are contacted in vitro and then are administered to the subject.

4. The method of claim 1, wherein the T-cells are contacted in vivo.

5. The method of claim 3, wherein the effective amount is below $10^{-8}$M.

6. The method of claim 4, wherein the effective amount is a blood concentration below $10^{-8}$M.

7. The method of claim 5, wherein the effective amount is between $10^{-10}$ and $10^{-16}$M.

8. The method of claim 6, wherein the effective amount is a blood concentration between $10^{-10}$ and $10^{-16}$M.

9. The method of claim 4, wherein the molecule is administered in conjunction with a different therapeutic agent that increases the CD4$^+$ count of HIV-infected patients.

10. The method of claim 1, wherein the human subject's T-cells are unable, prior to treatment with said molecule, to respond normally to T-cell proliferation-inducing stimuli.

11. The method of claim 4, wherein the molecule is administered in conjunction with an antigen.

12. The method of claim 1, 2, 3, 4, 5, 6, 7, 8, 9, 10, or 11, wherein the molecule mimics the site of a substrate recognized by a post-prolyl cleaving enzyme and includes a reactive group that binds covalently with a functional group in a reactive center of the post-prolyl cleaving portion of CD26.

13. The method of claim 12, wherein the molecule has the formula:

wherein B is boron; each $D_1$ and $D_2$ is, independently, a hydroxyl group or a group capable of being hydrolyzed to a hydroxyl group at physiological pH; Y is a group of the formula:

and each R1, R2, R3, R4, R5, R6, R7, and R8 is, independently, a group which does not significantly interfere with site specific recognition by DP-IV; and X comprises an amino acid or a peptide that mimics the site of a substrate recognized and that is cleave by CD26.

14. The method of claim 13, wherein the carbon bonded to boron is in an L-configuration.

15. The method of claim 1, wherein the carbon bonded to T is in an L-configuration.

16. The method of claim 1, wherein each of R1–R8 is an H.

17. The method of claim 1, wherein Y is a group of the formula:

* * * * *

UNITED STATES PATENT AND TRADEMARK OFFICE
CERTIFICATE OF CORRECTION

PATENT NO. : 6,503,882 B2
APPLICATION NO. : 09/484640
DATED : January 7, 2003
INVENTOR(S) : Huber et al.

It is certified that error appears in the above-identified patent and that said Letters Patent is hereby corrected as shown below:

In the Claims:

In Claim 1, at column 13, line 1, the structure

Should be replaced with the following structure:

In Claim 13, at column 14, line 50, delete "cleave" and replace with --cleaved--.

Signed and Sealed this

Eleventh Day of July, 2006

JON W. DUDAS
*Director of the United States Patent and Trademark Office*